(12) United States Patent
Bories

(10) Patent No.: US 10,655,916 B2
(45) Date of Patent: May 19, 2020

(54) METHOD FOR NON-DESTRUCTIVE TESTING FOR A REFRACTORY PART

(71) Applicant: SAINT-GOBAIN CENTRE DE RECHERCHES ET D'ETUDES EUROPEEN, Courbevoie (FR)

(72) Inventor: Olivier Bories, Avignon (FR)

(73) Assignee: SAINT-GOBAIN CENTRE DE RECHERCHES ET D'ETUDES EUROPEEN, Courbevoie (FR)

( * ) Notice: Subject to any disclaimer, the term of this patent is extended or adjusted under 35 U.S.C. 154(b) by 264 days.

(21) Appl. No.: 15/512,698

(22) PCT Filed: Sep. 14, 2015

(86) PCT No.: PCT/EP2015/070954
§ 371 (c)(1),
(2) Date: Mar. 20, 2017

(87) PCT Pub. No.: WO2016/041902
PCT Pub. Date: Mar. 24, 2016

(65) Prior Publication Data
US 2017/0284741 A1    Oct. 5, 2017

(30) Foreign Application Priority Data
Sep. 19, 2014 (FR) ..................... 14 58851

(51) Int. Cl.
G01N 33/38 (2006.01)
F27D 21/00 (2006.01)
G01N 22/02 (2006.01)
C03B 5/43 (2006.01)

(52) U.S. Cl.
CPC ......... *F27D 21/0021* (2013.01); *G01N 22/02* (2013.01); *G01N 33/388* (2013.01); *C03B 5/43* (2013.01)

(58) Field of Classification Search
CPC .................... F27D 21/0021; G01N 33/388
See application file for complete search history.

(56) References Cited

U.S. PATENT DOCUMENTS 5,363,106 A * 11/1994 Hosoda ............ G01N 33/388
                                                                342/22
2009/0221415 A1    9/2009 Avedikian et al.

FOREIGN PATENT DOCUMENTS

| FR | 2 689 245 A1 | 10/1993 |
|---|---|---|
| JP | H05-322800 A | 12/1993 |
| JP | H11-109045 A | 4/1999 |
| JP | 2001-526771 A | 12/2001 |
| JP | 2009-509898 A | 3/2009 |
| WO | 97/41449 A1 | 11/1997 |
| WO | 99/02979 A2 | 1/1999 |

OTHER PUBLICATIONS

English Translation Yutaka FR 2689245 B1 (Year: 1995).*
Takaichi et al., "Comparison of Antennas in Non-Destructive inspection," Another Ultrashort Pulse Radar Using Ultrashort Pulse Radar, p. 486, 2007. (Translation of relevant parts only).
Apr. 4, 2019 Office Action issued in Japanese Application No. 2017-515115.
Han, J. et al., "Ultra-Wideband Electronically Tumable Pulse Generators," IEEE Microwave and Wireless Components Letters, Mar. 2004, pp. 112-114, vol. 14, No. 3.
Carroll, B. et al., "Frequency-Modulated Continuous-Wave (FM-CW) Radar for Evaluation of Refractory Structures Used in Glass Manufacturing Furnaces," AIP Conference Proceedings, 2009, pp. 402-409, vol. 1096.
RST—The Radar Company, "Radar Systems Technology—Reaching Beyond Boundaries," Apr. 1, 2012, retrieved from http://www.rst-group-biz/uploads/media/RST_Broschuere_DE_01.pdf on Feb. 20, 2015.
Kharkovsky, S. et al., "Microwave Measurement of Refractory Materials at High-Temperature," AIP Conference Proceedings, 2009, pp. 1703-1710, vol. 1096.
Barnard, J, "Possible Non-Destructive Testing Method for Determining the Extent of Hydration in Magnesia-Based Refractory Bricks," The Southern African Institute of Mining and Metallurgy Refractories, 2010, pp. 117-128.
Nguyen, C. et al., "Design Concepts for a Miniature Pavement GPR Antenna," retrieved from http://d2dt15nnlpfr0r.cloudfront.net/tti.tamu.edu/documents/1341-3F.pdf on Feb. 20, 2015.
Fleischmann, B., "Non-destructive testing of refractories, especially AZS materials, with ultrasound, microwaves and gamma-radiation," Glastech. Ber. Glass Sci. Technol., 1995, pp. 259-265, vol. 68, No. 8.
Oct. 14, 2015 International Search Report issued in International Patent Appication No. PCT/EP2015/070954.

* cited by examiner

*Primary Examiner* — Jason L Vaughan
*Assistant Examiner* — Amanda Kreiling
(74) *Attorney, Agent, or Firm* — Oliff PLC

(57) ABSTRACT

A method for testing the internal structure of a refractory part, has the following steps: a) by a transmission antenna, sending at least one electromagnetic wave, termed a "pulse", into the refractory part to be tested; b) by a reception antenna, receiving the pulse after reflection thereof by a reflecting zone of the refractory part; c) analyzing the time offset between the two preceding steps in order to deduce the position, in the refractory part, of the reflecting zone, the pulse having a duration less than or equal to 0.5 nanoseconds.

10 Claims, 2 Drawing Sheets

| | Pulse duration | Central frequency | Observations for the block |
|---|---|---|---|
| Method A | 1 ns | 1.6 GHz |  |
| Visual observation | | |  |

| | Pulse duration | Frequency | Observations for the slab |
|---|---|---|---|
| Method A | 1 ns | 1.6 GHz |  |
| Method B | 0.1 ns | 6.0 GHz |  |
| Visual observation | | |  |

METHOD FOR NON-DESTRUCTIVE TESTING FOR A REFRACTORY PART

TECHNICAL FIELD

The invention relates to a nondestructive method for inspecting the internal structure of a refractory part.

PRIOR ART

Refractory products have various generally high-temperature applications. They generally take the form of large parts and may for example be used in glass melting furnaces.

Refractory parts may in particular be produced by fusion casting. This method consists in melting raw materials at very high temperatures in an arc furnace, then in pouring them into a mold. The molded part is then cooled and solidified. During this cooling step, shrinkage effects may occur and create cavities (defects) in the interior of the refractory parts.

Choice of a suitable composition and control of the manufacturing methods and of the quality of the raw materials allows high-quality refractory parts that are adapted to the various furnace regions in which they may be placed to be manufactured.

However, refractory parts undergo wear, in particular in certain critical, highly stressed regions, for example those making contact with the surface of the molten glass bath. Knowledge of the internal structure of the part makes it possible to ensure that it does not contain defects in these critical regions. Nondestructive inspecting methods are therefore used to evaluate the internal defects of refractory parts:

The ultrasonic method consists in measuring the attenuation of an ultrasound signal through a refractory part that is submerged in water. This method is very effective but it is most often implemented by positioning each refractory part in a water-filled tank.

Moreover, FR 2 689 245 discloses the use of ground penetrating radar (GPR).

However, there exists a blind spot, located directly under the antennae of the radar, that is several tens of millimeters in size and in which it is impossible to detect any defects, This method is therefore ineffective with all refractory parts of small thickness (slabs for example) because zones of potential defects and the blind spot overlap.

There is therefore a need for a nondestructive inspecting method not having these drawbacks, and in particular for a nondestructive inspecting method that is suitable for a refractory part of thickness smaller than 200 mm.

One aim of the invention is to at least partially meet this need.

SUMMARY OF THE INVENTION

The invention relates to a method for inspecting the internal structure of a refractory part, said method including the following steps;
 a) transmitting, by means of an emitting antenna, at least one electromagnetic wave, called the "pulse", into the refractory part to be inspected;
 b) receiving, by means of a receiving antenna, said pulse after it has been reflected by a reflecting zone of the refractory part; and
 c) analyzing the time shift between the two preceding steps in order to deduce therefrom the position, in the refractory part, of the reflecting zone, said pulse having a duration shorter than or equal to 0.5 nanoseconds.

The inventors have observed that such a duration advantageously allows the internal structure of the examined refractory part to be evaluated, even if this refractory part has a thickness smaller than 200 mm.

Preferably, a method according to the invention further has one or more of the following optional features:
 said duration is shorter than 0.3 nanoseconds, preferably shorter than 0.2 nanoseconds, or indeed shorter than 0.15 ns or than 0.10 ns;
 in step a), more than 1000 pulses per second are transmitted;
 the time interval between the emission of two pulses is larger than 100 ns;
 the pulse is a wave train the central frequency of which is preferably comprised between 2 and 10 GHz and preferably higher than 3 GHz:
 the emitting antenna and the receiving antenna are located at least 20 cm from one another, or indeed less than 10 centimeters from one another, or even less than 5 centimeters from one another;
 the refractory part has a thickness smaller than 300 millimeters, smaller than 200 millimeters, or even smaller than 100 millimeters;
 the refractory part is made of a sintered or fused material;
 the refractory part is made of a material that consists, for more than 90% of its weight, of one or more oxides chosen from the group made up of $ZrO_2$, $Al_2O_3$, $SiO_2$, $Cr_2O_3$, $Y_2O_3$, and $CeO_2$.

The method is preferably used to inspect the internal structure of a region of the refractory part that extends, from a surface of said refractory part, to a depth smaller than 200 mm.

The invention also relates to a method for manufacturing a furnace, in particular a glass furnace or a metallurgical furnace, said method including the following steps:
 A) Manufacturing a refractory part; and
 B) Inspecting the refractory part using an inspecting method according to the invention; and
 C) If the inspection is passed, placing the refractory part in the furnace, in particular in a region in which it is liable to make contact with molten metal or glass.

DEFINITIONS

Figure 1:
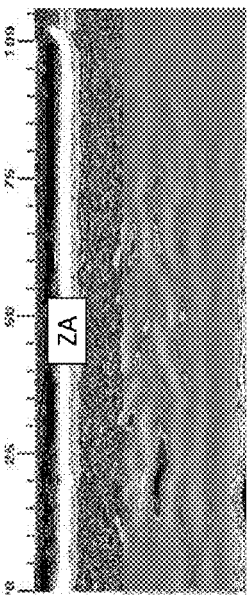
FIGS. 1-2 show results of observation of blocks according to the Examples.
Figure 1:
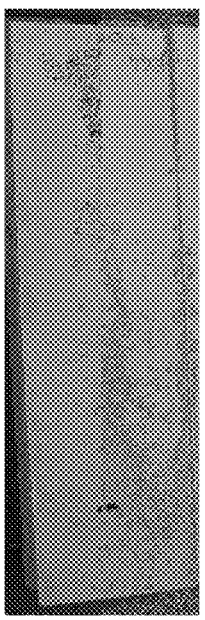

The thickness of a refractory part is here defined as its smallest dimension.
By "comprising a" or "including a", what is meant is "including at least one", unless otherwise indicated.

DETAILED DESCRIPTION

A method according to the invention implements the well-known principles of pulsed radar.

What are called "pulsed radar", or "radar à impulsions" in French, must be distinguished from continuous wave radar or "radar à onde continue ou à émission continue" in French, Specifically, the operating principles of these types of radar are very different: In particular, a pulsed radar emits a pulse and waits for its return. In contrast, a continuous wave radar continuously emits a wave from a first antenna and continuously receives the reflected wave using a second antenna.

Preferably, the method according to the invention implements a GPR technology, in particular the technology described in FR 2 689 245, only adapted to modify the nature of the electromagnetic waves transmitted into the refractory part. In particular, according to the invention, it is essential for the pulses to have a duration shorter than or equal to 0.5 nanoseconds, whereas FR 2 689 245 mentions only pulses having a width of 1 nanosecond.

A pulse may be made up of a signal of any shape, preferably one of sinusoidal, triangular, square, rectangular or sawtooth shape. Preferably the pulse is a periodic wave train that has a central frequency higher than 3 gigahertz, thereby improving resolution (i.e. the minimum distance required between two points to be able to distinguish them separately). The pulse may also be a non-periodic wave, for example a Dirac pulse.

The pulses are preferably emitted at regular intervals. Preferably, more than 1000 pulses are emitted per second. The emission frequency of the pulses must not be confused with the frequency of the wave that constitutes a pulse: 3 GHz for example.

In addition, the duration (or "width") of the pulses must not be confused with the period of the wave that constitutes a pulse. In particular, the inventors have discovered that, for a given period of the wave, a small pulse width makes it possible to improve the analysis of the surface region of a refractory part, and in particular to improve the analysis of the region of the refractory part that extends, from a surface of said refractory part, to a depth smaller than 200 mm.

Preferably, pulses are emitted in succession from various locations on the refractory part to be inspected. Preferably, the emitting antenna is moved over an exterior surface of the refractory part, for example one of the lateral faces of the refractory part. It is thus possible to obtain an image of the internal structure of the refractory part.

When the properties of the propagation medium of the electromagnetic waves change, and in particular in the case of variation in the dielectric constant of this medium, some of these waves are reflected. In particular, cavities in the interior of the refractory part may reflect the incident pulses. The reflected pulses may be recorded by the receiving antenna.

The emitting and receiving antennae may be identical or different.

In one preferred embodiment, the emitting antenna and the receiving antenna are placed side-by-side. By "side-by-side", what is meant is that the emitting antenna and receiving antenna make contact with one another or are separated from one another by a distance smaller than 5 centimeters. The compactness of the measuring device is improved thereby.

The emitting and receiving antennae may advantageously be placed in the same location, i.e. to reach the receiving antenna the reflected pulse passes through the zone passed through by the incident pulse immediately after it is emitted by the emitting antenna. The emitting and receiving antennae may also be placed in different locations.

Preferably, the emitting and receiving antennae are placed in contact with an exterior surface of the refractory part to be inspected. Preferably, the emitting antenna emits perpendicularly to said exterior surface of the refractory part and, more preferably, when the refractory part has a plane of symmetry, perpendicularly to said plane of symmetry.

In step c), the time shift makes it possible to know the position of the zone of the refractory part that reflected the incident pulse, the speed of the pulse in the refractory part being easily determined. If this position corresponds to an exterior surface of the refractory part, no defect has been detected. Otherwise, the refractory part contains a structural heterogeneity that may be considered to be a defect.

The analysis carried out in step c) allows the internal structure of the inspected refractory part to be evaluated. Preferably, step c) allows representations and in particular images of this internal structure to be obtained.

For deep regions of the refractory part, the precision of the information obtained by the analysis of step c) is similar to that obtained with conventional pulsed radar. In contrast, the information delivered in step c) for surface regions is reliable, unlike the information obtained with conventional pulsed radar.

If a hidden defect is identified, the refractory part may be rejected, for example in order to be scrapped or recycled. Otherwise, it may be used and for example placed in a glass furnace. in particular in a critical region.

EXAMPLES

The following examples are provided for illustrative purposes and do not limit the invention.

A block of dimensions 250 mm×500 mm×1200 mm and a slab of dimensions 50 mm×500 mm×600 mm, which are obtained by a method in which raw materials were melted in an arc furnace, then poured into a mold and solidified, were analyzed by means of a method implementing GPR technology, using two pulse durations of 1 ns ("method A"), and of 0.1 ns according to the invention ("method B"). Method A was representative of the prior art.

In each of the two methods, electromagnetic waves were emitted by a pulsed radar: a StructureScan Mini™ radar from the company GSSI for method A and the Groundvue 5C radar from the company Utsi Electronics for method B. The waves of the signals were imperfect square waves. Each pulse was a pulse train made up of a multitude of sinusoidal waves the frequencies of which could vary by plus or minus 60 to 70% about the central frequency, which was for example comprised between 2 and 10 GHz for method B. The duration and central frequency of the pulses are given in tables 1 and 2.

The block and the slab were placed on their main face (the face of 500 mm×1200 mm size and the face of 500 mm×600 mm size, respectively) and the radar was moved along the opposite surface. Each of the block and the slab was then sawn in the transverse plane of symmetry of their main face to allow visual observation of defects and to allow this observation to be compared to the images obtained with the two methods.

Figure 2:
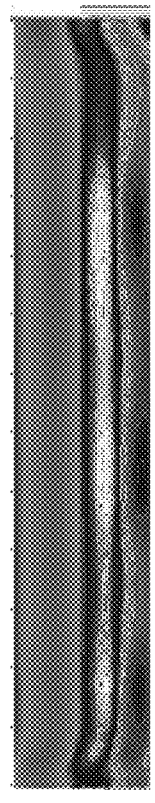
Figure 2:
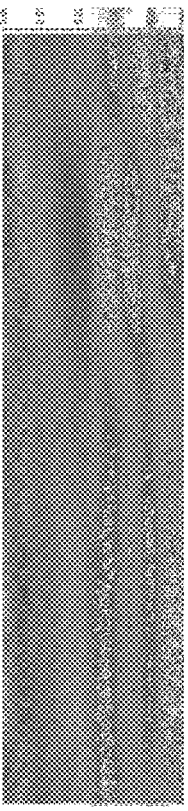
Figure 2:
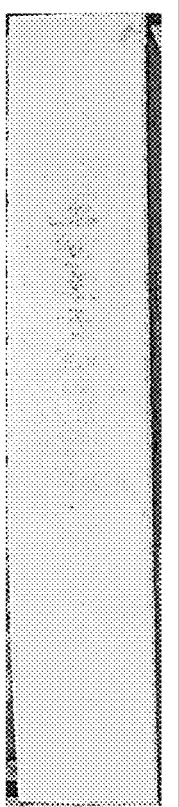

FIGS. 1 and 2 present the results of the observations.

It may be seen that the use of the radar at 1.6 GHz and with a pulse duration of one nanosecond leaves a blind spot ZA on the edge of the image of the block and is ineffective for the slab. In particular, the zone of defects (black spots corresponding to porosities in the visual observation) does not appear at all in the image of the slab.

In contrast, with method B, white zones that correspond to the zone of defects are seen to appear. It may moreover be noted that the resolution of the image obtained with this method is very good.

As should now be clearly apparent, the invention provides a method that is simple to implement, and that in particular does not require the refractory part to be inspected to be immersed, and that is effective over all the thickness of the refractory part. This method is particularly suitable for the inspection of refractory parts of small thickness such as slabs.

Of course, the invention is not limited to the described embodiments, which were nonlimiting and provided by way of illustration.

The invention claimed is:

1. A method for inspecting the internal structure of a refractory part made of a fused material and that consists, for more than 90% of its weight, of one or more oxides selected from the group consisting of $ZrO_2$, $Al_2O_3$, $SiO_2$, $Cr_2O_3$, $Y_2O_3$, and $CeO_2$, said refractory part having a thickness smaller than 300 millimeters, said method including the following steps:
   a) transmitting, by means of an emitting antenna, at least one electromagnetic wave, called the "pulse", into the refractory part to be inspected;
   b) receiving, by means of a receiving antenna, said pulse after it has been reflected by a reflecting zone of the refractory part; and
   c) analyzing the time shift between the two preceding steps in order to deduce therefrom the position, in the refractory part, of the reflecting zone, said pulse having a duration shorter than or equal to 0.5 nanoseconds.

2. The method as claimed in claim 1, wherein the duration is shorter than 0.2 nanoseconds.

3. The method as claimed in claim 1, wherein the pulse is a wave train that has a central frequency higher than 3 gigahertz.

4. The method as claimed in claim 1, wherein, in step a), more than 1000 pulses per second are transmitted or wherein two successive pulses are separated by more than 100 ns.

5. The method as claimed in claim 1, wherein the emitting antenna and the receiving antenna are side-by-side.

6. The method as claimed in claim 1, wherein the refractory part has a thickness smaller than 200 millimeters.

7. The method as claimed in claim 1, wherein, if no hidden defects are identified in step c), the refractory part is placed in a furnace.

8. The method as claimed in claim 7, wherein the refractory part is placed in a region of the furnace in which the refractory part is liable to make contact with molten metal or glass.

9. A method for inspecting the internal structure of a refractory part made of a fused material and that consists, for more than 90% of its weight, of one or more oxides selected from the group consisting of $ZrO_2$, $Al_2O_3$, $SiO_2$, $Cr_2O_3$, $Y_2O_3$, and $CeO_2$, said refractory part having a thickness smaller than 300 millimeters, said method including the following steps:
   a) transmitting, by means of an emitting antenna, at least one electromagnetic wave, called the "pulse", into the refractory part to he inspected;
   b) receiving, by means of a receiving antenna, said pulse after it has been reflected by a reflecting zone of the refractory part; and
   c) analyzing the time shift between the two preceding steps in order to deduce therefrom the position, in the refractory part, of the reflecting zone, said pulse having a duration shorter than or equal to 0.5 nanoseconds, and the pulse being a wave train the central frequency of which is comprised between 2 GHz and 10 GHz.

10. The method as claimed in claim 9, wherein the pulse is a wave train that has a central frequency between 3 GHz and 10 GHz.

* * * * *